United States Patent [19]

Gazzi et al.

[11] 4,163,652

[45] Aug. 7, 1979

[54] REFRIGERATIVE FRACTIONATION OF CRACKING-GASES IN ETHYLENE PRODUCTION PLANTS

[75] Inventors: Luigi Gazzi, Milan; Oronzo Sguera, San Donato Milanese, both of Italy

[73] Assignee: Snamprogetti S.p.A., Milan, Italy

[21] Appl. No.: 781,064

[22] Filed: Mar. 24, 1977

[30] Foreign Application Priority Data

Mar. 26, 1976 [IT] Italy .................. 21580 A/76

[51] Int. Cl.² ................................................ F25J 3/02
[52] U.S. Cl. ........................................ 62/28; 62/39; 62/26; 62/31; 62/40
[58] Field of Search ............... 62/23, 27, 28, 39, 40, 62/26, 30, 31

[56] References Cited

U.S. PATENT DOCUMENTS

| | | | |
|---|---|---|---|
| 2,731,810 | 1/1956 | Hachmuth | 62/28 |
| 2,775,103 | 12/1956 | Koble et al. | 62/28 |
| 2,823,523 | 2/1958 | Eakin et al. | 62/28 |
| 2,909,905 | 10/1959 | Mitchell et al. | 62/40 |
| 2,938,934 | 5/1960 | Williams | 62/28 |
| 2,960,838 | 11/1960 | Denton | 62/39 |
| 3,073,129 | 1/1963 | Grenier | 62/28 |
| 3,367,122 | 2/1968 | Tutton | 62/28 |
| 3,433,026 | 3/1969 | Swearingen | 62/38 |
| 3,756,036 | 9/1973 | Ezell | 62/28 |

*Primary Examiner*—Norman Yudkoff
*Attorney, Agent, or Firm*—Morgan, Finnegan, Pine, Foley & Lee

[57] ABSTRACT

In a method for the refrigerative fractionation of cracking gases in ethylene production plants, the improvement consisting in that ethane is used as the refrigeration fluid, it being thus possible to attain very low temperatures, down to minus 88° C.: concurrently, the condensation with water is practicable whenever water is available in large masses at a temperature which is in the range from zero centigrade to +25° C.; that is the case of sea waters in cold countries or fresh waters in cold climate. A considerable first-cost and running economy become thus available.

7 Claims, 6 Drawing Figures

REFRIGERATIVE FRACTIONATION OF CRACKING-GASES IN ETHYLENE PRODUCTION PLANTS

This invention relates to a method for the refrigerative fractionation of cracking-gases in an ethylene production plant.

It is known that the fractionation of the cracking-gases in the ethylene-producing installations requires that low temperatures may be attained, the lowest temperature in the installation being within the range between minus 100° C. and minus 150° C.

In order that such temperatures may be reached, up to three cascaded refrigerating cycles have been adopted heretofore, the refrigeration fluid being propylene for the cycle at the highest temperature, ethylene for the intermediate temperature cycle and methane for the lowest temperature cycle.

Subsequently there has been, a tendency towards replacing the refrigeration supplied by the methane cycle by the refrigeration as supplied by the expansion and vaporization of a few processing streams, produced in the liquid state and containing high amounts of methane.

The suppression of the methane refrigerating cycle as a discrete and independent unit has effected a considerable simplification in the processes, so that the present-day installations, which are based on the use of two refrigeration cycles with propylene and ethylene, are considerably more convenient to operate and also cheaper.

Contrarily to what has heretofore been believed and applied by the conventional art, it has been found that it is possible further to reduce the number of refrigeration cycles if ethane is used as the refrigerating fluid.

As a matter of fact, it is possible, with ethane, to reach very low temperatures, of about minus 80° C., it being concurrently possible to carry out the condensation with water if water is available at a comparatively low temperature, say between 0° C. and +25° C.

The ethane cycle thus encompasses a temperature range from minus 88° C. to +25° C., which is narrower than that which is usually supplied by the two propylene and ethylene cascade cycles which cover a range of from minus 100° C. to +40° C.

It has been found, also, that the refrigeration made available by processing streams previously employed in the prior art in the temperature range below minus 100° C., can be extended so as to fulfil the requirements of the fractionation of the cracking-gases at temperature from minus 88° C. to still lower temperatures.

Among the systems which can be employed for producing such an additional refrigeration, there can be mentioned by way of example and without limitation, those using the expansion of the hydrogen fraction in a turbine, those using the expansion in a turbine of the methane fraction as produced from the head of the demethanization unit, the expansion in a turbine of both the hydrogen and the methane fractions, the production in the liquid state of the processing streams which contain high proportions of methane, the latter to be expanded through a valve and to be vaporized at low pressures.

In the cold and temperate climate areas, cooling waters at a low temperature are available. This is the case, for example, with the seawater off the coasts of Northern Europe or off the coasts of the southernmost portion of South America, or with underground waters in the temperate regions, whenever used in continuous-flow cooling systems rather than for topping-up cooling towers.

Whenever low-temperature cooling water is unavailable, the condensation of ethane may be caused to occur in a system which exploits low-level power which cannot be exploited otherwise.

In the ethylene-producing installations such a power source is constituted by the flue gases of the cracking ovens, such gases being discharged in the atmosphere at a temperature in the range between +180° C. and +250° C.

It has been found that the sensible heat of the flue gases affords the following alternatives:

To produce low-pressure steam to be used as a motive fluid in injectors or steam turbines which drive compressors: in both cases, water cooled under vacuum is produced, which has a temperature in the range between 0° C. to 20° C.;

To produce either low-pressure steam or hot water, to be used in refrigeration plants of the absorption type, using ammonia or lithium salts: the refrigeration supplied by such installations can be used for the condensation of ethane.

In the ensuing description, reference will be had to an ethylene-producing installation according to the present invention, which is based on the following refrigerating "chain":

cold water, at 8° C.
refrigeration cycle with ethane
expansion of the hydrogen fraction in a turbine The disclosure has been restricted to those component parts of the installation which are modified by the invention, the other components parts having been omitted since they are known to those skilled in the art.

The raw material for the production of ethylene, such as ethane, but any other raw material can be considered, is cracked in the thermal decomposition ovens.

The effluent from the ovens is quenched, cooled and compressed to the usual pressure, such as 35 abs. atmospheres.

During progress of the compression stage, the effluent from the ovens, that is the raw gas, is stripped of the acidic gaseous components. Upon compression, it is stripped of acetylene and dehydrated.

Figure 1:
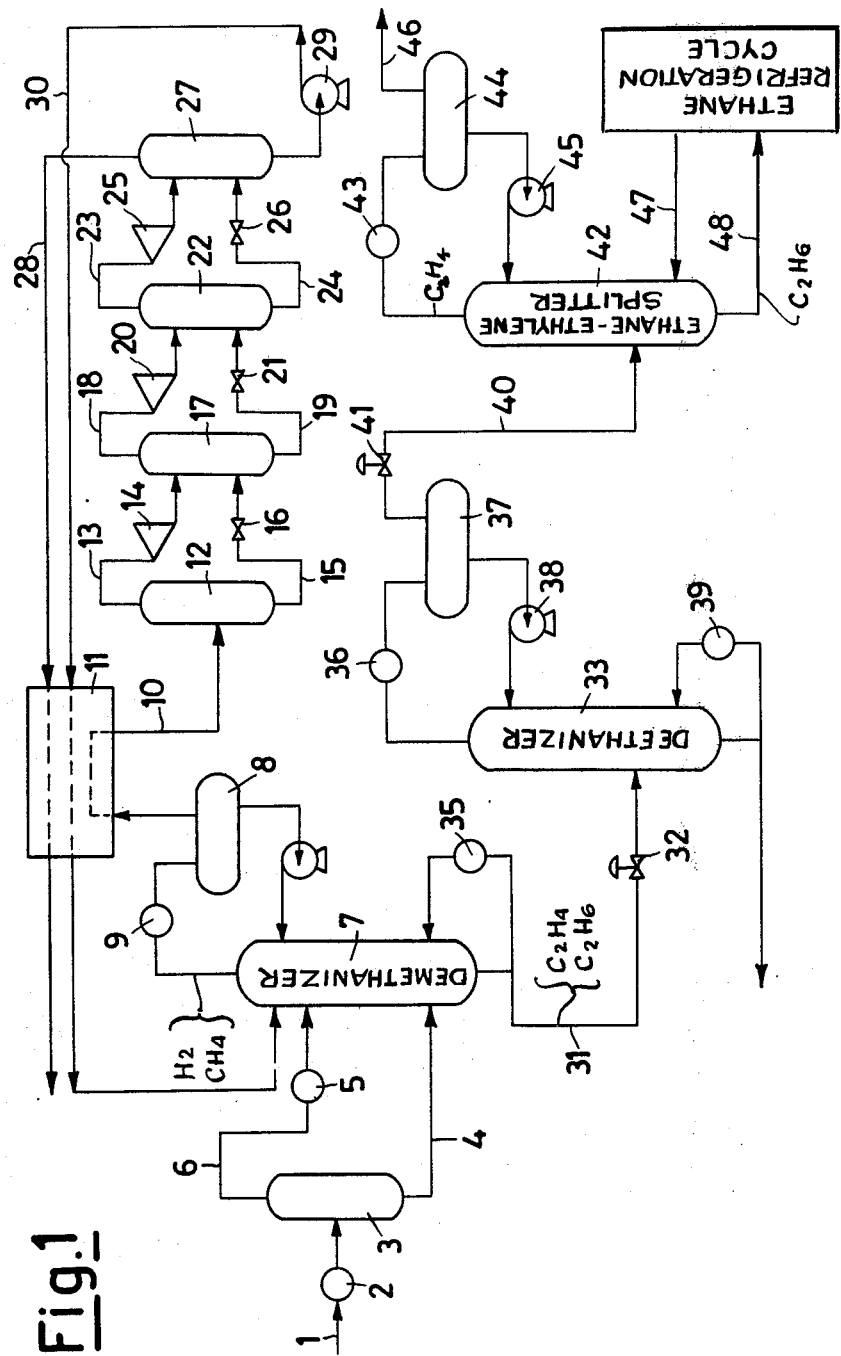
FIG. 1 is a diagram of fractionation apparatus adapted for use in the practice of our invention.

At this stage, it enters the fractionation area, as shown in FIG. 1.

The gas, introduced through the piping 1, is cooled to minus 30° C. in the ethane refrigerator 2 (the conventional frigorie recovery stages, the frigories being those of the processing streams, have been omitted for the sake of simplicity in the area which is involved in the refrigeration of the ethane cycle), a liquid being produced which is separated at 3 and is fed, via the piping 4, to the demethanizing unit 7.

The gas emerging from the top of the separator 3, via the piping 6, is cooled down to minus 59° C. in the ethane refrigeration unit 5 and then fed to the demethanizing unit 7.

The condenser 9 of the demethanizing unit 7 is cooled with refrigerating ethane down to minus 82° C.

The head product emerging from the storage tank 8 contains hydrogen, methane and considerable amounts of ethylene and ethane: it is cooled in the frigorie-recovering unit 11 and then partially liquefied and sent through the piping 10 into the separator 12.

The gas is sent through the piping 13 to the first stage of the turbine, 14, wherein it is caused to expand, while the liquid, through the piping 15, is caused to expand in the valve 16. The gas and the liquid after their relative expansions are sent to the separator 17.

The expansions are repeated (for a total of three times in the example shown) until reaching the final pressure in the separator 27, that which corresponds to a saturation temperature of minus 146° C. approximately.

From 27 the gas, which contains hydrogen and methane, is sent through the main 28, to a number of frigorie-recovering units 11 (only the first has been shown) and is then heated up to the ambient temperature.

The liquid, by means of the pump 29 and through the piping 30, is also preheated in the frigorie-recovery unit 11 and then fed into the demethanizing unit 7 as a top feeding stream.

The bottom product of the demethanizing unit 7, the latter being equipped with a reboiler 35, is fed through the piping 31, to the deethanizing unit 33 after having been expanded in the valve 32.

The deethanizing unit 33 is a quite conventional column which is equipped with the condenser 36, the reflux storage tank 37, the reflux pump 38, the reboiler 39. From the top of the column ethylene plus ethane are obtained and from its bottom, the C3 and heavier components are obtained, to be sent either to burnout or to a subsequent fractionation stage.

The distillate of the deethanizing unit 33 is sent via the piping 40 to the ethylene-ethane splitter 42, after having been expanded in the valve 41.

The splitter column 42 can be of conventional make, equipped with a condenser which is refrigerated with boiling ethane at minus 41° C., and having also a reboiler heated with ethane which is condensed at about 0° C.

Nonetheless, and this is an integral part of this invention, the splitter column 42 can be integrated with the ethane refrigeration cycle, dispensing with the reboiler and taking the ethane vapors from the refrigeration cycle under a pressure of about 17.8 abs. atmospheres which corresponds to a saturation temperature of minus 12° C.

This fact involves savings both in terms of power and installation costs.

Figure 2:
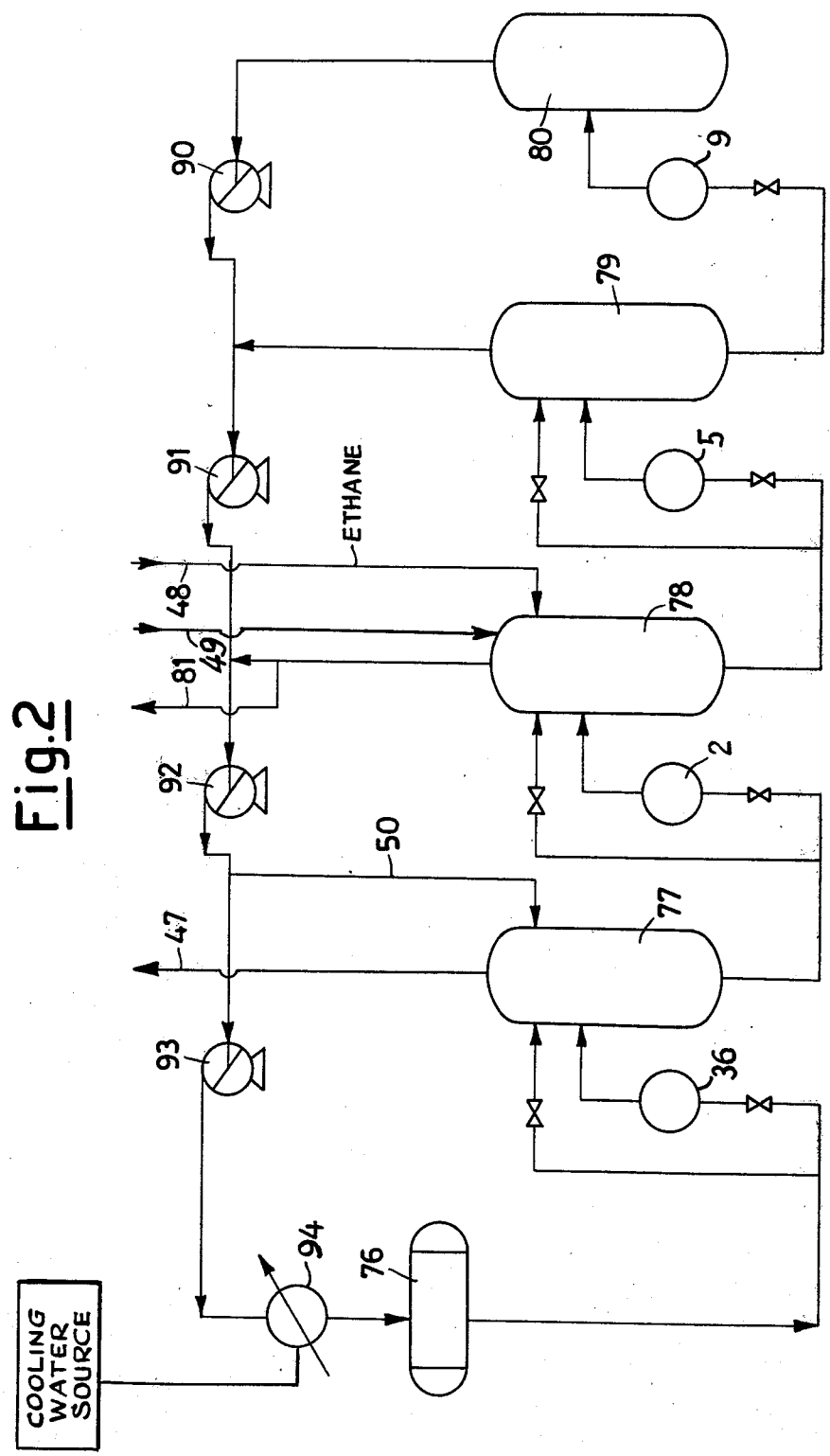
FIG. 2 is a diagram of the ethane refrigeration cycle.

The ethane refrigeration cycle which integrates the installation now described, is shown in FIG. 2. It is composed by four compression stages which correspond to four temperature levels, namely:

1st stage: 1.06 abs.atmospheres—88° C.
2nd stage: 3.00 abs.atmospheres—65° C.
3rd stage: 7.52 abs.atmospheres—41° C.
4th stage: 17.8 abs.atmoshperes—12° C.
delivery: 38.00 abs.atmospheres+18° C. condensation The selection of the number of the stages is a merely economic question. As a rule, it can be stated that the number of the stages can be varied from three to six.

Figure 3:
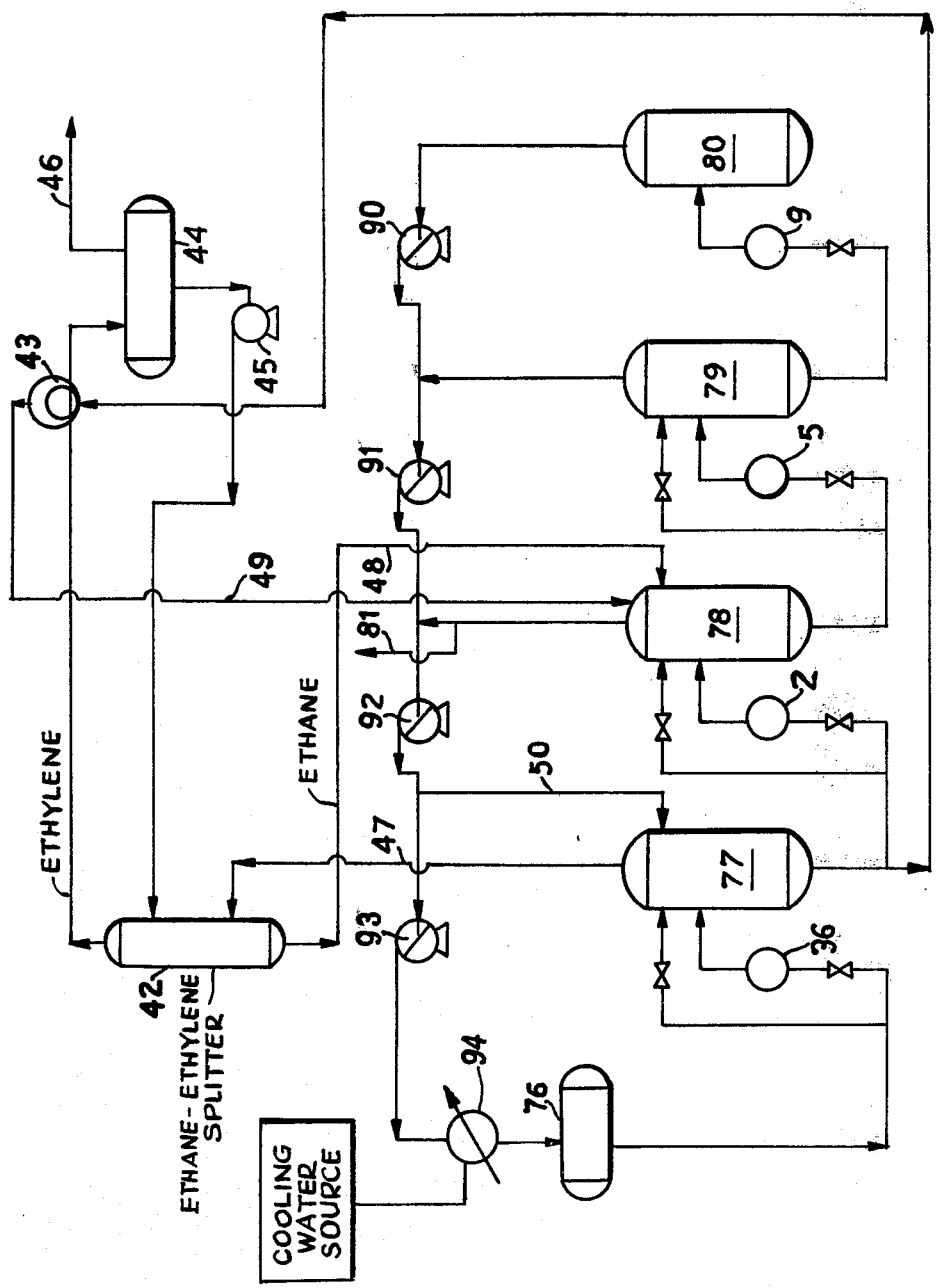
FIG. 3 is a diagram showing the connection of the refrigeration cycle illustrated in FIG. 2 with the fractionation apparatus illustrated in FIG. 1.

The refrigeration cycle is quite conventional, with the exception of the interconnection with the splitter, this detail being better described in FIG. 3.

With reference to FIGS. 2 and 3, wherein the same reference numerals correspond to like component parts, liquid ethane at minus 41° C. is drawn from the refrigeration cycle and exactly from the bottom of the separator 77, and vaporized in the condenser 43 of the splitter, 77, thus producing the reflux stream which is required for the operation of the splitter as such. The thus produced vapors are recycled to the refrigeration cycle via the piping 49, and precisely to the separator 78 and then to the compressor 92.

Additionally, ethane vapors are compressed in the third stage of the refrigeration compressor 92, together with other vapors of the cycle. A fraction of this stream is drawn and is saturated in the separator 77 and then sent, via the piping 47, to the splitter 42, such vapors having in this case the function of boil-up vapors. The balance of the stream from compressor 92 flows to compressor 93 and then to condenser 94 where it is condensed, utilizing water from the cooling water source (conventional apparatus for the vacuum condensation of low pressure steam produced by means of the heat of flue gases from cracking ovens or conventional absorption type of refrigeration apparatus utilizing ammonia or lithium salts and low pressure steam or hot water produced by means of the heat of flue gases from cracking ovens).

From the bottom of the splitter 42 emerges a stream of liquid ethane, which is the summation of the as produced ethane plus the condensed boil-up, which, through the piping 48, is returned to the refrigeration cycle and exactly to the separator 78.

The as-produced ethane is drawn from the refrigeration cycle in the state of vapor and under a pressure of 7.6 abs.atm., through the piping 81.

Figure 4:
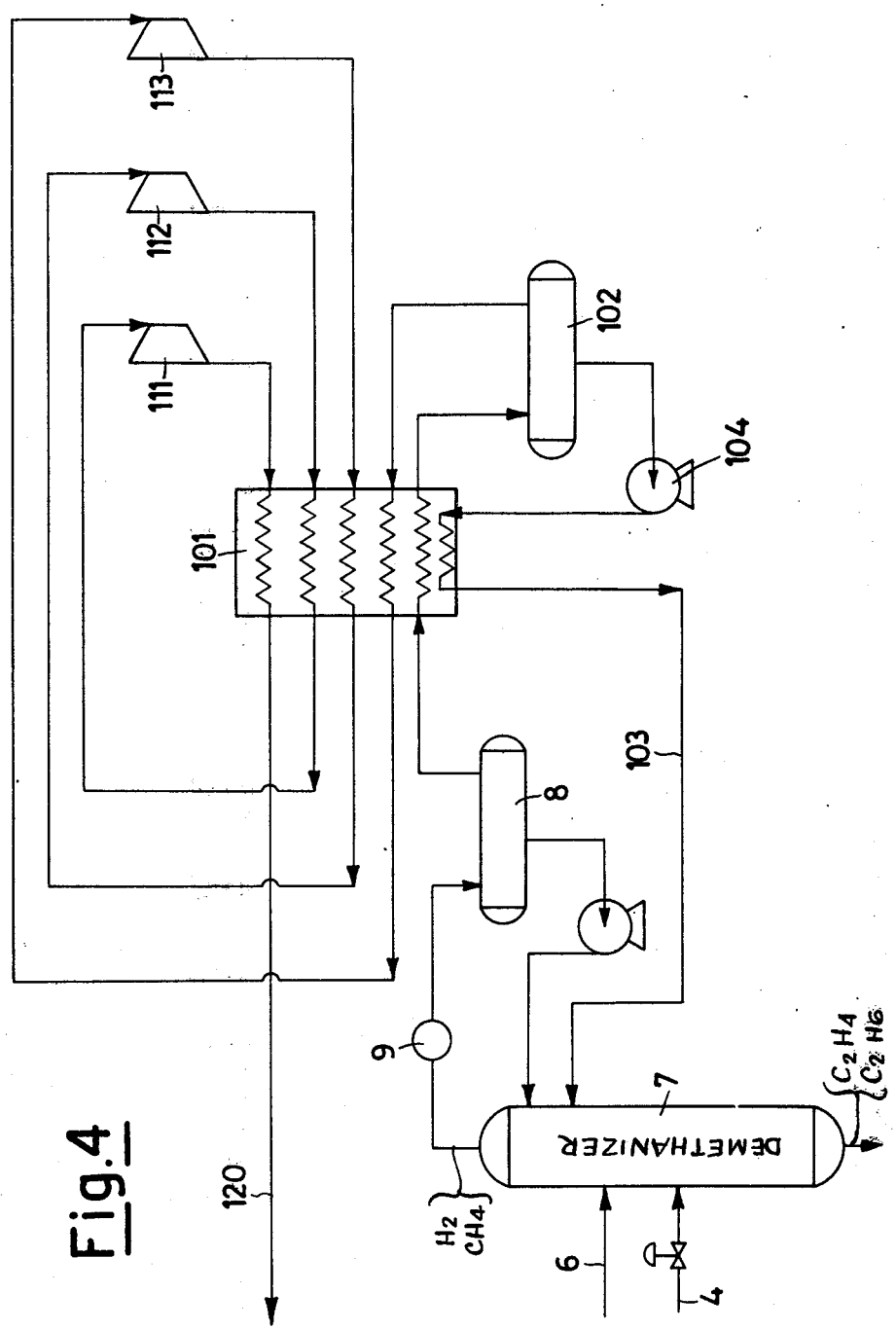
FIG. 4 is a diagram of a modification of the apparatus illustrated in FIG. 1.

As a possible further example of refrigeration below minus 88° C., the diagram of FIG. 4 is reported, which uses a turbo-expanding machine which, differently from the turbine of FIG. 1, works in the superheated-gas field.

The mixture of the distillate of the demethanizing unit 7 coming from the reflux storage tank 8 is pre-cooled in the frigorie-recovery unit 101 and sent to the separator 102. From 102 the liquid, which is essentially methane and contains the last residues of ethylene and ethane, is sent back to the demethanizing unit 7 via the piping 103 and by means of the pump 104, thus recovering frigories in the exchanger 101. The gas, which is essentially hydrogen, is superheated in the frigorie-recovering unit 101 and then caused to expand in the first stage of the turbine 113.

The operation is repeated (a total of three times in FIG. 4, being it understood that the number of the expansion stages is but an example and can be varied for reasons of mechanical construction and economical considerations) until reaching the final pressure of the hydrogen fraction, the latter being drawn through the piping 120.

Whenever it is desired to produce the hydrogen fraction under a high pressure, the refrigeration due to the turbo-expansion of the hydrogen is no longer available. In this case, FIG. 5, the raw gas is introduced in the installation via the piping 1, is cooled to minus 59° C.

with ethane in the refrigerating unit 2 and the condensed liquid is separated in the separator 3 and fed to the demethanizing unit 7 through the piping 4.

The residual gas in the separator 3 is cooled with ethane in the refrigerating unit 5. The condensed liquid, in its turn, is separated in the separator 201 and fed to the demethanizing unit 7 through the piping 202. The demethanizing unit 7 is equipped with a condenser 204, the latter being cooled with boiling ethane under atmospherical pressure.

A fraction of the liquid condensed in the reflux storage tank 205 is sent back as a reflux stream to the demethanizing unit 7 through the pump 206.

A second liquid stream, through the piping 207, is undercooled in the frigorie recovery unit 210 and then caused to expand in the valve 211 and set to two frigorie-exploiting units at extremely low temperatures, that is, the frigorie recovery unit 210 and the dephlegmator 215.

Figure 5:
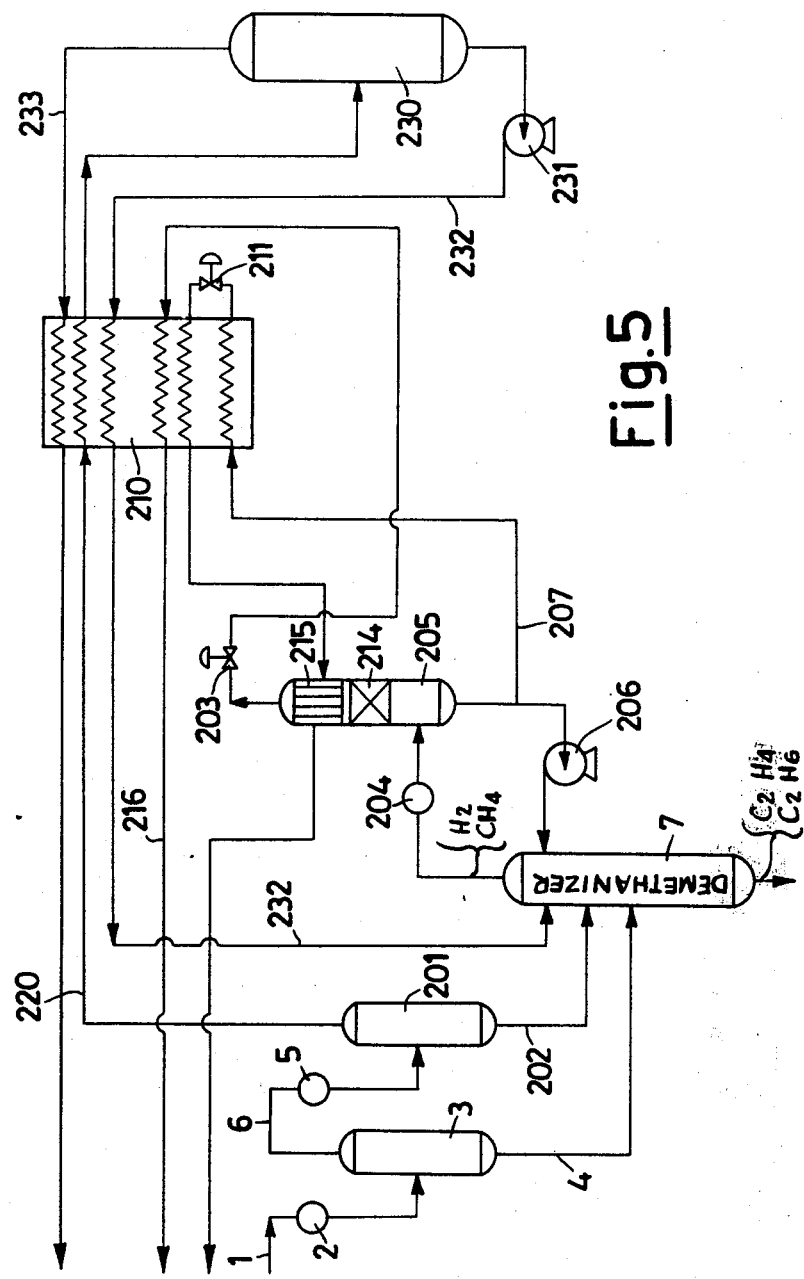
FIG. 5 is a diagram of a further modification of the apparatus illustrated in FIG. 1.

After vaporization in these two units, the stream is cooled in various frigorie-recovery units now shown in FIG. 5 for the sake of simplicity, and is recycled to the raw gas compressor.

The gas which has been separated in the reflux storage tank 205 is stripped of the residual ethylene and ethane in the packing 214 by the agency of the reflux as produced in the dephlegmator 215. Upon such a purification, the distillate from the demethanizing unit, which is the methane fraction, is heated, after having previously been expanded in the valve 203, in the frigorie recovery unit 210 and in various other frigorie recovery units not shown in FIG. 5, and delivered to the installation terminals via the piping 216.

The gas separated in the separator 201, and which contains hydrogen, methane, ethylene and ethane, is sent via the piping 220 to the frigorie recovery unit 210, thus producing a liquid fraction to be separated in the separator 230.

The latter liquid fraction, which contains methane, and ethane, is sent back to the demethanizing unit 7 via the piping 232 by means of the pump 231 and after having been heated in the frigorie recovery unit 210.

The gas which composes the hydrogen fraction, after having been heated in the frigorie recovery unit 210 and other units not shown in the drawings, is delivered via the piping 233 to the installation terminals.

Figure 6:
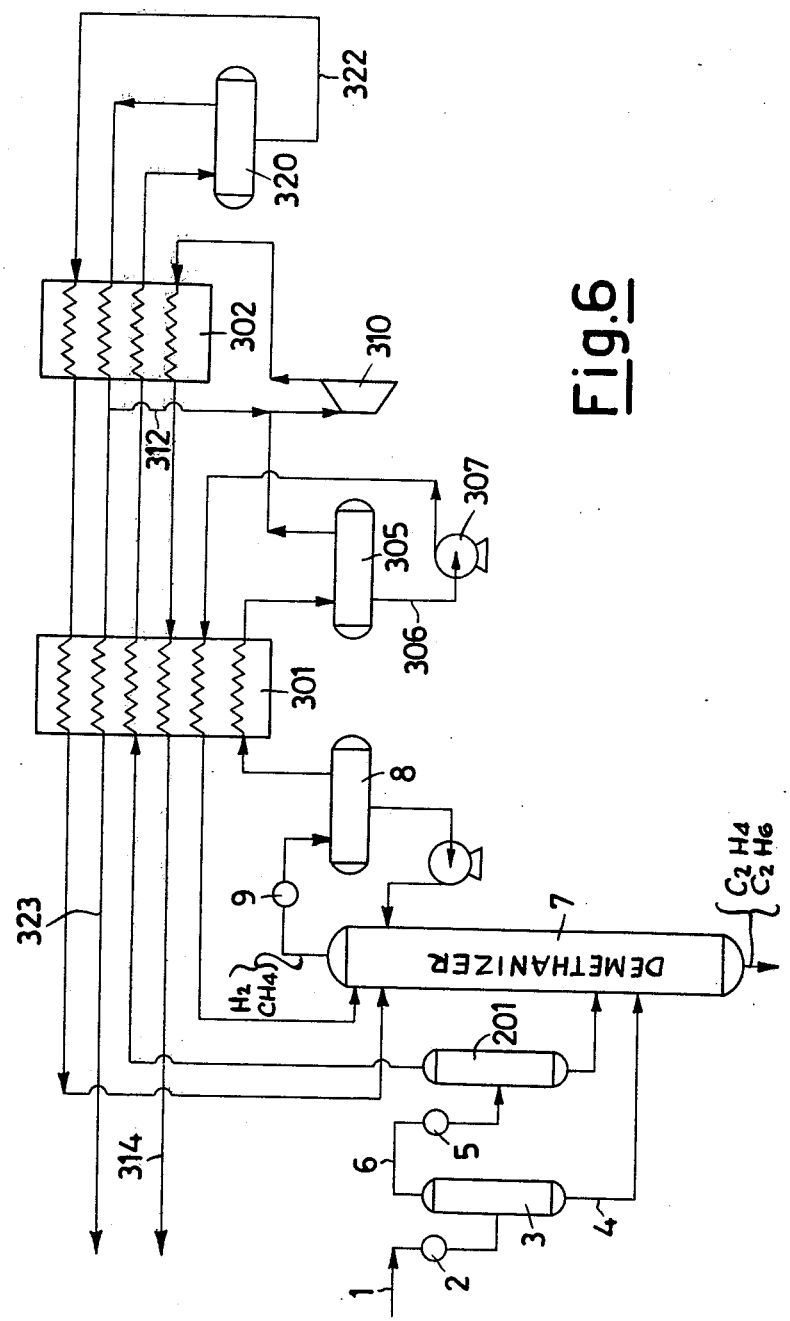
FIG. 6 is a diagram of a further modification of the apparatus illustrated in FIG. 1.

Another diagram for achieving the cooling to temperatures below minus 88° C., and which can be adopted when the raw gas contains significant amounts of methane (that is, when the raw materials sent to cracking are heavier than ethane, for example propane, naphtha or fuel-oil), is shown in FIG. 6.

This diagram exploits the turboexpansion of the methane fraction as produced at the head of the demethanizing unit.

The distillate of the demethanizing unit, emerging from the replux storage tank 8, is cooled in the frigorie recovery unit 301 and sent to the separator 305. The liquid, which contains the ultimate fractions of ethylene and ethane, is sent back to the demethanizing unit 7 via the piping 306 by means of the pump 307, but after having previously been heated in the frigorie recovery unit 301.

The gas emerging from the separator 305, and which composes the methane fraction, is sent to the turboexpansion unit 310 and subsequently heated in the frigorie recovery units 302 and 301 and in other like units not shown in the drawings and delivered to the installation terminals through the piping 314. The residual gas in the separator 201, which contains hydrogen, methane, ethylene and ethane, is cooled in the frigorie recovery units 301 and 302 to be sent to the separator 320 wherein a liquid is separated which, via the piping 322, is sent back to the demethanizing unit 7.

The gas in the separator 320, which is the hydrogen fraction, is also heated in the frigorie recovering units 302 and 301 and in other like units not shown in the drawings and delivered at the installation terminals via the piping 323.

If necessary, a portion of the as-produced hydrogen can be combined with the methane fraction through the piping 312 in order to increase the number of available frigories.

An example will now be given in order to better illustrate the invention without, however, limiting it.

EXAMPLE

Having now reference to FIG. 1, the installation is fed through the piping 1, with 32,169 kilograms an hour of a gas mixture under the pressure of 32.2 abs. atmospheres and at a temperature of 15° C., having the following composition:

| | | |
|---|---|---|
| $H_2$ | 1133 | kilogram/hour |
| CO | 163 | " |
| $CH_4$ | 1311 | " |
| $C_2H_4$ | 15375 | " |
| $C_2H_6$ | 12989 | " |
| $C_3H_4$ | 7 | " |
| $C_3H_6$ | 571 | " |
| $C_3H_8$ | 66 | " |
| $C_4H_8$ | 195 | " |
| $C_4H_{10}$ | 96 | " |
| $C_{5+}$ | 263 | " |

Upon cooling in the ethane refrigerating unit 2, the temperature of the mixture is brought to minus 34° C. and the separator 3 separates the liquid phase from the gaseous one.

The gaseous phase emerging from the head of the separator 3 under the pressure of 32.0 abs. atmospheres, has the following composition:

| | | |
|---|---|---|
| $H_2$ | 1100 | kilograms an hour |
| CO | 155 | " |
| $CH_4$ | 1131 | " |
| $C_2H_4$ | 8975 | " |
| $C_2H_6$ | 5909 | " |
| $C_3H_4$ | 2 | " |
| $C_3H_6$ | 129 | " |
| $C_4H_8$ | 6 | " |
| $C_4H_{10}$ | 5 | " |
| $C_{5+}$ | 1 | " |

This gaseous phase, through the piping 6, is cooled to minus 59° C. in the ethane refrigerating unit 5 and then fed to the demethanizing unit 7.

The liquid emerging from the bottom of the separator 3 has the following composition:

| | | |
|---|---|---|
| $H_2$ | 23 | kilograms an hour |
| CO | 8 | " |
| $CH_4$ | 180 | " |
| $C_2H_4$ | 6400 | " |
| $C_2H_6$ | 7080 | " |
| $C_3H_4$ | 5 | " |
| $C_3H_6$ | 442 | " |
| $C_3H_8$ | 58 | " |

|   |   |   |
|---|---|---|
| $C_4H_8$ | 189 | " |
| $C_4H_{10}$ | 91 | " |
| $C_{5+}$ | 262 | " |

This liquid is fed to the demethanizing unit 7 via the piping 4. The head stream of the demethanizing unit 7, said unit working with 60 plates and with a reflux ratio of 0.6 is condensed in the condenser 9 with refrigerating ethane down to a temperature of minus 82° C.

At the outlet of the storage tank 8 a gaseous stream is obtained which has the following composition:

|   |   |   |
|---|---|---|
| $H_2$ | 1133 | kilograms an hour |
| CO | 165 | " |
| $CH_4$ | 1533 | " |
| $C_2H_4$ | 1763 | " |
| $C_2H_6$ | 285 | " |

Such a stream is cooled in the frigorie recovering unit 11 and then partially liquefied and sent, via the piping 10, to the separator 12.

The gas is sent to the first stage, 14, of the turbine to be expanded therein, thwereas the liquid is caused to expand in the valve 16. Both the gas and the liquid, after the respective expansions, are sent to the separator 17.

The expansions are repeated for a total of three times and the specifications of the liquid and gaseous streams emerging from the separators 12,17,22,27 are tabulated below:

| Separator 12 | gas | | liquid | |
|---|---|---|---|---|
| $H_2$ | 1,131 | kgs/hr | 2 | kgs/hr |
| CO | 162 | " | 3 | " |
| $CH_4$ | 1,361 | " | 172 | " |
| $C_2H_4$ | 644 | " | 1,119 | " |
| $C_2H_6$ | 34 | " | 251 | " |

Temperature: minus 110° C. - Pressure: 30.5 abs. atmospheres

| Separator 17 | gas | | liquid | |
|---|---|---|---|---|
| $H_2$ | 1,132 | kgs/hr | 1 | kg/hr |
| CO | 162 | " | 3 | " |
| $CH_4$ | 1,350 | " | 183 | " |
| $C_2H_4$ | 495 | " | 1,268 | " |
| $C_2H_6$ | 23 | " | 262 | " |

Temperature: minus 120° C. - Pressure: 17.6 abs. atmospheres

| Separator 22 | gas | | liquid | |
|---|---|---|---|---|
| $H_2$ | 1,133 | kgs/hr | 0 | kg/hr |
| CO | 163 | " | 2 | " |
| $CH_4$ | 1,334 | " | 199 | " |
| $C_2H_4$ | 360 | " | 1,373 | " |
| $C_2H_6$ | 15 | " | 270 | " |

Temperature: minus 135° C. - Pressure: 10.0 abs. atmospheres

| Separator 27 | gas | | liquid | |
|---|---|---|---|---|
| $H_2$ | 1,133 | kgs/hr | 0 | kgs/hr |
| CO | 163 | " | 2 | " |
| $CH_4$ | 1,307 | " | 226 | " |
| $C_2H_4$ | 93 | kgs/hour | 1,670 | kgs/hour |
| $C_2H_6$ | 8 | " | 277 | " |

Temperature: minus 146° C. - Pressure: 5.6 abs. atmospheres

The gas stream emerging from the separator 27, after that frigories have been recovered, is delivered to the installation terminals, whereas the liquid stream is pumped back to the demethanizing unit 7.

The bottom liquid stream of the demethanizing unit 7, having a temperature of minus 1° C. and a pressure of 31.5 abs. atmospheres has the following composition:

|   |   |   |
|---|---|---|
| $H_2$ | 0 | kgs/hour |
| CO | 0 | " |
| $CH_4$ | 4 | " |
| $C_3H_4$ | 15,282 | " |
| $C_3H_6$ | 12,981 | " |
| $C_3H_4$ | 7 | " |
| $C_3H_6$ | 571 | " |
| $C_3H_8$ | 66 | " |
| $C_4H_8$ | 195 | " |
| $C_4H_{10}$ | 96 | " |
| $C_{5+}$ | 263 | " |

This liquid is sent to the deethanizing unit 33 which works with 40 plates and with a reflux ratio equal to 0.3, after having been expanded up to a pressure of 29 abs. atmospheres.

The distillate from the deethanizing unit 33 has at a temperature of minus 7° C. and under a pressure of 28.5 abs.atm. the following composition:

|   |   |   |
|---|---|---|
| $H_2$ | 0 | kgs/hour |
| CO | 0 | " |
| $CH_4$ | 4 | " |
| $C_2H_4$ | 15,272 | " |
| $C_2H_6$ | 12,831 | " |
| $C_3H_4$ | 0 | " |
| $C_3H_6$ | 70 | " |
| $C_3H_8$ | 2 | " |
| $C_4H_8$ | — | |
| $C_4H_{10}$ | — | |
| $C_{5+}$ | — | |

This distillate, after having been expanded in the valve 41 to a pressure of 17.8 abs.atm. is sent to the ethylene-ethane splitter 42.

From the bottom of the deethanizing column 33 a bottom stream is obtained which has the following composition:

|   |   |   |
|---|---|---|
| $H_2$ | 0 | kgs/hour |
| CO | 0 | " |
| $CH_4$ | 0 | " |
| $C_2H_4$ | 10 | " |
| $C_2H_6$ | 150 | " |
| $C_3H_4$ | 7 | " |
| $C_3H_6$ | 501 | " |
| $Ca_3H_8$ | 64 | " |
| $C_4H_8$ | 195 | " |
| $C_4H_{10}$ | 96 | " |
| $C_{5+}$ | 263 | " |

From the splitter, which works with 100 plates and a reflux ratio of 4, a head product is obtained as a stream at the pressure of 16.9 abs.atm. and temperature of minus 43.5° C., which has the following composition:

|   |   |   |
|---|---|---|
| $H_2$ | 0 | kgs/hour |
| CO | 0 | " |
| $CH_4$ | 4 | " |
| $C_2H_4$ | 15,000 | " |
| $C_2H_6$ | 15 | " |
| $C_3H_4$ | — | |
| $C_2H_4$ | — | |
| $C_3H_8$ | — | |
| $C_4H_8$ | — | |
| $C_4H_{10}$ | — | |
| $C_{5+}$ | — | |

The bottom product is a liquid at the pressure of 17.8 abs.atm. and a temperature of minus 13.9° C. and has the following composition:

| | | |
|---|---|---|
| H₂ | — | |
| CO | — | |
| CH₄ | — | |
| C₂H₄ | 272 | kgs/hour |
| C₂H₆ | 12,816 | " |
| C₃H₄ | 0 | " |
| C₃H₆ | 70 | " |
| C₃H₈ | 2 | " |
| C₄H₈ | — | |
| C₄H₁₀ | — | |
| C₅₊ | — | |

The liquid is sent to the refrigerating circuit.

We claim:

1. A process for the refrigerative fractionation of the cracking gases containing hydrogen, methane, ethylene, ethane and higher molecular weight hydrocarbons in plants for the production of ethylene, which comprises refrigerating said cracking gases to form a liquid fraction and a gas fraction, separating the liquid fraction from the gas fraction, further refrigerating the gas fraction, feeding said liquid fraction and the further refrigerated gas fraction to a demethanizing stage, recovering hydrogen and methane together with relevant amounts of ethylene and ethane from said demethanizing stage as overhead and recovering ethylene and ethane together with higher molecular weight products from said demethanizing stage as bottom product, condensing a part of said overhead product by refrigeration and feeding said condensed portion to a reflux storage tank, refluxing a condensed portion of the overhead from the reflux storage tank to said demethanizing stage, cooling the uncondensed portion of said overhead, subjecting said uncondensed portion of overhead to a series of expansion and separation stages in order to recover ethylene and ethane therefrom, recycling said recovered ethylene and ethane to said demethanizing stage, distilling said bottom product so that a stream of ethylene and ethane is separated therefrom, feeding said separated stream of ethylene and ethane to an ethylene-ethane splitter and then recovering ethylene from said splitter through an associated condenser as overhead and recovering ethane from said splitter as bottom product, and supplying refrigeration by subjecting a refrigerating fluid consisting of ethane recovered as bottom product from said splitter and fed to an ethane refrigerating cycle comprised of a series of compression and expansion stages, and condensing said refrigerating ethane after the last compression stage, so as to produce a refrigeration effect down to the boiling temperature of −88° C. of ethane at atmospheric pressure, wherein cooling water having a temperature in the range of from 0° to 25° C. is utilized in condensing said refrigerating ethane.

2. A process as claimed in claim 1, wherein the cooling water utilized for condensing ethane is obtained under vacuum from the condensation of low pressure steam produced by means of the sensible heat of flue gases withdrawn from the cracking ovens at a temperature in the range of from 180° C. to 250° C. after utilization as motive fluid in injectors or steam turbines.

3. A process as claimed in claim 1, wherein the cooling water utilized for condensing ethane is cooled by a refrigeration plant of the absorption type utilizing ammonia or lithium salts and low-pressure steam or hot water is produced by means of the sensible heat of flue gases withdrawn from the cracking ovens.

4. A method as claimed in claim 1, wherein said condenser associated with the ethylene-ethane splitter is cooled with ethane coming from said ethane refrigeration cycle.

5. A method as claimed in claim 1, wherein uncondensed overhead from the demethanizing stage is utilized in a further refrigeration stage in which the temperature is reduced to a temperature below that attained by said ethane refrigerating cycle and in the range of from −120° C. to −150° C. by feeding uncondensed overhead from said demethanizing stage to a frigorie unit at a pressure in the range of from 30 to 35 absolute atmospheres to cool said uncondensed overhead and form a liquid fraction and a gaseous fraction, expanding said gaseous fraction in a turbine and expanding said liquid fraction through a valve so that further liquid fraction and a further gaseous fraction are created, and repeating said expansion process until a pressure in the range of from 2 to 7 absolute atmospheres is reached, and then returning the liquids obtained thereby to said demethanizing stage through said frigorie recovery unit, and withdrawing the residual gaseous fraction through said frigorie recovery unit.

6. A method as claimed in claim 1, wherein an additional refrigeration process is carried out by the following combination of steps:

(a) refrigerating the raw gas supplied at a pressure of 20 to 35 absolute atmospheres in two or more stages, of which the last stage is the atmospheric stage of the ethane cycle, thereafter separating a gaseous fraction from a liquid fraction, feeding said liquid fraction to the demethanizing unit, cooling said gaseous fraction to a temperature in the range of from −120° C. to −150° C. in a frigorie recovery unit, separating out a condensed liquid, heating said liquid in the frigorie recovery unit to set free a vapor forming a hydrogen fraction heated in the frigorie recovery unit and feeding said liquid to the demethanization unit; and (b) Cooling the reflux condenser of the demethanizing unit with the atmospheric stage of the methane refrigeration cycle to produce a liquid rich in methane, feeding a portion of said liquid to the demethanizing unit as reflux, cooling the residue thereof in a frigorie recovery unit and expanding said residue through a valve to about 2–3 absolute atmospheres and utilizing said expanded residue as refrigerating fluid in said recovery unit, and feeding vapors from the reflux tank of the demethanizing unit to a packing and than a dephlegmator cooled by vaporizing and further heating said methane rich stream and then recycling said stream to the cracking-gas compressor after further heating.

7. A method as claimed in claim 1, wherein an additional refrigeration process is carried out by the following combination of steps:

(a) refrigerating the raw gas supplied at a pressure of 20 to 35 absolute atmospheres in two or more stages, of which the last stage is the atmospheric stage of the ethane cycle, thereafter separating a gaseous fraction from a liquid fraction, feeding said liquid fraction to the demethanizing unit, cooling said gaseous fraction to a temperature in the range of from −120° C. to −150° C. in a frigorie recovery unit, separating out a condensed liquid, heating said liquid in the frigorie recovery unit to set free a vapor forming a hydrogen fraction heated in the frigorie recovery unit and feeding said liquid to the demethanization unit; and (b) cooling the distillate from the reflux storage tank of the demthanizing unit in a first frigorie-recovery unit, separating the condensed liquid in a separator, sending said condensed liquid back to the demethanizing unit after recovering frigories therefrom in the first frigorie-recovery unit, expanding the gaseous stream which forms the methane fraction, together with a portion of the hydrogen stream which has been previously heated in the second frigorie-recovery unit, in a turbine in one or more stages, so that said gaseous streams are cooled and supplies the frigories which are required for the two recovery units.

* * * * *

UNITED STATES PATENT AND TRADEMARK OFFICE
CERTIFICATE OF CORRECTION

PATENT NO. : 4,163,652
DATED : August 7, 1979
INVENTOR(S) : Gazzi, et al.

It is certified that error appears in the above-identified patent and that said Letters Patent are hereby corrected as shown below:

Col. 5, line 16, after "and" change "set" to --sent--.

Col. 7, line 25, after "therein" change "thwereas" to --whereas--.

Col. 8, lines 5-8 change "$C_3H_4$     to    --$C_2H_4$
$C_3H_6$             $C_2H_6$
$C_3H_4$             $C_3H_4$
$C_3H_6$"           $C_3H_6$--.

line 45, change "$Ca_3H_8$" to --$C_3H_8$--.

line 49, after the table (lines 38-48) and before the paragraph beginning "From the splitter," insert --Pressure: 29 abs. atmospheres and temperature 72°C.-- line 53, change "43.5" to --34.5--.

UNITED STATES PATENT AND TRADEMARK OFFICE
CERTIFICATE OF CORRECTION

PATENT NO. : 4,163,652
DATED : August 7, 1979
INVENTOR(S) : Gazzi, et al.

It is certified that error appears in the above-identified patent and that said Letters Patent are hereby corrected as shown below:

Col. 8, line 62, change "$C_2H_4$" (second occurrence in table) to --$C_3H_6$--.

Col. 10, line 51, after "and" change "than" to --then--.

Signed and Sealed this

First Day of July 1980

[SEAL]

Attest:

SIDNEY A. DIAMOND

Attesting Officer          Commissioner of Patents and Trademarks